(12) United States Patent
Roux et al.

(10) Patent No.: US 8,014,493 B2
(45) Date of Patent: Sep. 6, 2011

(54) METHOD AND DEVICES FOR ASSESSING THE THREAT STATUS OF AN ARTICLE AT A SECURITY CHECK POINT

(75) Inventors: Michel Roux, Quebec (CA); Dan Gudmundson, Quebec (CA); Michel R. Bouchard, Saint-Augustin-de-Desmaures (CA); Vinh Phuc Pham, Donnacona (CA); Alexandre Filiatrault, Quebec (CA); Sebastien Roy, Quebec (CA); Steve Godbout, L'Ancienne-Lorette (CA)

(73) Assignee: Optosecurity Inc., Quebec, Quebec (CA)

( * ) Notice: Subject to any disclaimer, the term of this patent is extended or adjusted under 35 U.S.C. 154(b) by 0 days.

(21) Appl. No.: 12/680,622

(22) PCT Filed: Sep. 30, 2008

(86) PCT No.: PCT/CA2008/001721
§ 371 (c)(1),
(2), (4) Date: Sep. 22, 2010

(87) PCT Pub. No.: WO2009/043145
PCT Pub. Date: Apr. 9, 2009

(65) Prior Publication Data
US 2011/0007870 A1    Jan. 13, 2011

Related U.S. Application Data

(60) Provisional application No. 61/094,743, filed on Sep. 5, 2008, provisional application No. 61/097,060, filed on Sep. 15, 2008.

(30) Foreign Application Priority Data

Oct. 1, 2007  (CA) ................ PCT/CA2007/001749

(51) Int. Cl.
*G01N 23/083*   (2006.01)
*G01N 23/10*    (2006.01)

(52) U.S. Cl. ............ 378/56; 378/57; 378/207; 378/208
(58) Field of Classification Search ............ 378/56, 378/57, 207, 208
See application file for complete search history.

(56) References Cited

U.S. PATENT DOCUMENTS
3,589,511 A    6/1971  Britt
(Continued)

FOREIGN PATENT DOCUMENTS
CA    2 574 402 A1    1/2006
(Continued)

OTHER PUBLICATIONS
International Search Report: PCT CA2007/001658 Jan. 10, 2008.
(Continued)

*Primary Examiner* — Edward J Glick
*Assistant Examiner* — Thomas R Artman
(74) *Attorney, Agent, or Firm* — Ladas & Parry LLP

(57) ABSTRACT

A method for performing security screening at a checkpoint is provided. The method includes providing an X-ray imaging system having a scanning area and providing a supporting device for supporting articles to be scanned in the scanning area, wherein the supporting device has at least two reference areas manifesting respective X-ray signatures when exposed to X-rays, the X-ray signatures being distinguishable from one another. The method further includes placing an article to be scanned on the supporting device, introducing the article to be scanned in the scanning area while the article is supported by the supporting device and using the X-ray imaging system for deriving the X-ray signatures of the reference areas and for obtaining an X-ray image of the article while the supporting device is in the scanning area. The method further includes using the X-ray signatures to derive X-ray attenuation information from the X-ray image and using the X-ray attenuation information in determining if the article is a security threat.

21 Claims, 13 Drawing Sheets

U.S. PATENT DOCUMENTS

| | | |
|---|---|---|
| 3,609,045 A | 9/1971 | Stein |
| 3,673,394 A * | 6/1972 | Hartmann ............... 702/172 |
| 4,392,237 A | 7/1983 | Houston |
| 4,454,949 A | 6/1984 | Flum |
| 4,864,142 A | 9/1989 | Gomerg |
| 4,870,666 A | 9/1989 | Lonn et al. |
| 4,962,515 A | 10/1990 | Kopans |
| 4,974,247 A | 11/1990 | Friddell |
| 4,985,906 A | 1/1991 | Arnold |
| 5,044,002 A | 8/1991 | Stein |
| 5,056,124 A | 10/1991 | Kakimoto et al. |
| 5,400,381 A | 3/1995 | Steude et al. |
| 5,428,657 A | 6/1995 | Papanicolopoulos et al. |
| 5,442,672 A | 8/1995 | Bjorkholm et al. |
| 5,490,218 A | 2/1996 | Krug et al. |
| 5,557,108 A | 9/1996 | Tumer |
| 5,568,262 A | 10/1996 | LaChapelle et al. |
| 5,600,303 A | 2/1997 | Husseiny et al. |
| 5,600,700 A | 2/1997 | Krug et al. |
| 5,692,029 A | 11/1997 | Husseiny et al. |
| 5,768,334 A | 6/1998 | Maitrejean et al. |
| 5,838,758 A | 11/1998 | Krug et al. |
| 5,864,600 A | 1/1999 | Gray et al. |
| 6,018,562 A | 1/2000 | Willson |
| 6,026,171 A | 2/2000 | Hiraoglu et al. |
| 6,054,712 A | 4/2000 | Komardin et al. |
| 6,069,936 A | 5/2000 | Bjorkholm |
| 6,542,574 B2 | 4/2003 | Grodzins |
| 6,654,445 B2 | 11/2003 | Shepherd et al. |
| 6,707,381 B1 | 3/2004 | Maloney |
| 6,707,879 B2 | 3/2004 | McClelland et al. |
| 6,721,387 B1 | 4/2004 | Naidu et al. |
| 6,721,391 B2 | 4/2004 | McClelland et al. |
| 6,763,083 B2 | 7/2004 | Fernandez |
| H2110 H | 10/2004 | Newman |
| 6,840,120 B2 | 1/2005 | Sakairi et al. |
| 6,952,163 B2 | 10/2005 | Huey et al. |
| 7,065,175 B2 | 6/2006 | Green |
| 7,092,485 B2 | 8/2006 | Kravis |
| 7,164,750 B2 | 1/2007 | Nabors et al. |
| 7,257,188 B2 | 8/2007 | Bjorkholm |
| 7,274,768 B2 | 9/2007 | Green |
| 7,317,390 B2 | 1/2008 | Huey et al. |
| 7,355,402 B1 | 4/2008 | Taicher et al. |
| 7,386,093 B2 | 6/2008 | Wu et al. |
| 7,614,788 B2 | 11/2009 | Gatten |
| 7,789,401 B2 * | 9/2010 | Ambrefe, Jr. ............ 280/47.34 |
| 2001/0033636 A1 | 10/2001 | Hartick et al. |
| 2003/0062373 A1 | 4/2003 | Holland |
| 2004/0016271 A1 | 1/2004 | Shah et al. |
| 2004/0101097 A1 | 5/2004 | Wakayama et al. |
| 2004/0252024 A1 | 12/2004 | Huey et al. |
| 2005/0036689 A1 | 2/2005 | Mahdavieh |
| 2005/0058242 A1 | 3/2005 | Peschmann |
| 2005/0111618 A1 | 5/2005 | Sommer, Jr. et al. |
| 2005/0117700 A1 | 6/2005 | Peschmann |
| 2005/0173284 A1 | 8/2005 | Ambrefe, Jr. |
| 2005/0193648 A1 | 9/2005 | Klein et al. |
| 2006/0078085 A1 | 4/2006 | Zanker |
| 2006/0086794 A1 | 4/2006 | Knowles et al. |
| 2006/0115044 A1 | 6/2006 | Wu et al. |
| 2006/0193434 A1 | 8/2006 | Green |
| 2006/0203960 A1 | 9/2006 | Schlomka et al. |
| 2006/0257005 A1 | 11/2006 | Bergeron et al. |
| 2007/0003009 A1 | 1/2007 | Gray |
| 2007/0013519 A1 | 1/2007 | Chung et al. |
| 2007/0041612 A1 | 2/2007 | Perron et al. |
| 2007/0041613 A1 | 2/2007 | Perron et al. |
| 2007/0058037 A1 | 3/2007 | Bergeron et al. |
| 2007/0132580 A1 | 6/2007 | Ambrefe, Jr. |
| 2007/0133743 A1 | 6/2007 | Johnson et al. |
| 2007/0192850 A1 | 8/2007 | Cowburn |
| 2007/0217571 A1 | 9/2007 | Teslyar et al. |
| 2007/0297560 A1 | 12/2007 | Song et al. |
| 2008/0062262 A1 | 3/2008 | Perron et al. |
| 2008/0116267 A1 | 5/2008 | Barber |
| 2008/0138475 A1 | 6/2008 | Heuft |
| 2008/0152082 A1 | 6/2008 | Bouchard et al. |
| 2008/0170660 A1 | 7/2008 | Gudmundson et al. |
| 2008/0240578 A1 | 10/2008 | Gudmundson et al. |
| 2008/0312768 A1 | 12/2008 | Ewing et al. |
| 2009/0060135 A1 | 3/2009 | Morton |
| 2009/0146061 A1 | 6/2009 | Manneschi |
| 2009/0168963 A1 | 7/2009 | Harding |
| 2009/0196396 A1 * | 8/2009 | Doyle et al. ............ 378/53 |
| 2010/0027741 A1 * | 2/2010 | Doyle et al. ............ 378/57 |
| 2011/0007870 A1 | 1/2011 | Roux et al. |

FOREIGN PATENT DOCUMENTS

| | | |
|---|---|---|
| CA | 2 623 812 A1 | 5/2007 |
| CA | 2666838 A1 | 3/2008 |
| CA | 2676913 A1 | 3/2008 |
| GB | 2 420 683 A | 5/2006 |
| GB | 2 441 551 A | 3/2008 |
| GB | 2 441 551 | 4/2010 |
| JP | 2006-214725 A | 8/2006 |
| WO | PCT/CA2009/000401 | 1/2001 |
| WO | 03/052398 A1 | 6/2003 |
| WO | 2006/119603 A1 | 11/2006 |
| WO | 2008/009134 A1 | 1/2008 |
| WO | 2008/034232 A1 | 3/2008 |
| WO | 2008/040119 A1 | 4/2008 |
| WO | 2008/119151 A1 | 10/2008 |
| WO | 2009/024818 A1 | 2/2009 |
| WO | 2009/046529 A1 | 4/2009 |
| WO | 2009/114928 A1 | 9/2009 |
| WO | WO2009/127353 A1 | 10/2009 |
| WO | 2010/025538 A1 | 3/2010 |
| WO | 2010/025539 A1 | 3/2010 |
| WO | 2010/028474 A1 | 3/2010 |
| WO | WO2010/145016 A1 | 12/2010 |

OTHER PUBLICATIONS

Written Opinion PCT/CA2007/001658 Jan. 10, 2008.
Informal Communication With the Applicant PCT/CA2007/001658 Sep. 22, 2008.
International Preliminary Report on Patentability PCT/CA2007/001658 Dec. 17, 2008.
International Search Report: PCT/CA2007/001749 Jan. 14, 2008.
International Search Report: PCT/CA2008/001591 Nov. 20, 2008.
Written Opinion PCT/CA2008/001591 Nov. 20, 2008.
International Search Report: PCT/CA2008/001721 Dec. 4, 2008.
Written Opinion: PCT/CA2008/001721 Dec. 4, 2008.
International Search Report: PCT/CA2008/001792 Dec. 5, 2008.
Written Opinion: PCT/CA2008/001792 Dec. 5, 2008.
International Preliminary Report on Patentability: PCT/CA2008/001792 Feb. 1, 2010.
International Search Report: PCT/CA2008/002025; Jun. 4, 2009.
Written Opinion: PCT/CA2008/002025 Jun. 4, 2009.
International Search Report: PCT/CA2008/000395 Jul. 6, 2009.
Written Opinion: PCT/CA2008/000395 Jul. 6, 2009.
International Search Report: PCT/CA2008/000401 Aug. 6, 2009.
Written Opinion PCT/CA2008/000401 Aug. 6, 2009.
International Search Report: PCT/CA2009/000811 Nov. 10, 2009.
Written Opinion PCT/CA2009/000811 Nov. 10, 2009.
International Preliminary Report on Patentability PCT/CA2007/001749 Apr. 7, 2009.
Canadian Office Action mailed Jul. 29, 2009 Canadian Patent App. 2,651,728.
Canadian Office Action mailed Jul. 10, 2009 Canadian Patent App. 2,666,838.
Canadian Office Action mailed Nov. 3, 2009 Canadian Patent App. 2,666,838.
Canadian Office Action mailed Jan. 28, 2010 Canadian Patent App. 2,676,913.
Canadian Office Action mailed Jan. 28, 2010 Canadian Patent App. 2,666,838.
R. Benjamin; "Object-Based 3D X-Ray Imaging for Second-line Security Screening", London, 1995 (exact date not given) Abstract Only.
PinPoint TM Threat Identification Software, http://www.guardiantechintl.com/security.php?npage=pinpoint, Jul. 25, 2005 4 pages.

"Secure Flight Passenger Screening Program", http://www.globalsecurity.org/security/systems/passenger_screen.htm, Oct. 28, 2005, 6 pages.

Optosecurity; "Security Technology Overview: Advanced Vehicle Verification & Threat Identification", 1 page.

Airport Magazine, Solutions, Products, Services, vol. 7, Mar. 2006, 5 Pages.

D.L.Page, et al.; "Perception-based 3D Triangle Mesh Segmentation Using Fast Marching Watersheds", Proc. Intl. Conf. on Computer Vision and Pattern Recognition, vol. II, pp. 27-32, Madison, WI, Jun. 2003 (exact date not given).

Freud, et al; "Simulation of X-ray NDT Imaging Techniques", Proceedings of the 15$^{th}$ World Conference on Non-Destructive Testing, Rome, Oct. 15-21, 2000, http://www.ndt.net/article/wcndt00/papers/idn256/idn256.htm, pp. consulted Dec. 3, 2009, 7 pages.

Xie,et al; "Simulation of X-ray Imaging Systems for Luggage Inspection", Second Explosives Detection Symposium and Aviation Security Conference, Nov. 12-15, 1996, pp. 248-253.

Canadian Patent Appln. 2,676,903 Office Action mailed Mar. 2, 2010.

Canadian Patent Appln. 2,651,728 Office Action mailed Mar. 19, 2010.

Canadian Patent Appln. 2,690,163 Office Action mailed Mar. 31, 2010.

Canadian Patent Appln. 2,676,913 Office Action mailed May 5, 2010.

International Preliminary Report on Patentability of International Patent Appln. PCT/CA2008/001721 mailed on Apr. 15, 2010.

Written Opinion of the International Patent Appln. PCT/CA2007/001749 mailed Jan. 14, 2008.

Canadian Office Action issued May 14, 2010 in connection with Canadian Patent Application No. 2,690,831.

Canadian Office Action issued Jun. 7, 2010 in connection with Canadian Patent Application No. 2,692,662.

Canadian Office Action issued Jun. 28, 2010 in connection with Canadian Patent Application No. 2,697,525.

Canadian Office Action issued Jun. 30, 2010 in connection with Canadian Patent Application No. 2,696,031.

USPTO OA mailed Sep. 30, 2010 in connection with U.S. Appl. No. 12/311,031.

USPTO OA mailed Aug. 12, 2010 in connection with U.S. Appl. No. 12/311,522.

USPTO OA mailed Aug. 5, 2010 in connection with U.S. Appl. No. 12/385,253.

Canadian OA mailed Aug. 31, 2010 in connection with Canadian Appln. 2,690,831.

Canadian OA mailed Aug. 31, 2010 in connection with Canadian Appln. 2,692,662.

Written Opinion of the International Searching Authority of International Patent Application PCT/CA2010/000916, Optoscusity Inc. et al.

International Search Report of International Patent Application PCT/CA2010/000916, Optosecurity Inc. et al.

International Preliminary Report on Patentability of International Patent Application PCT/CA2008/001591, Optosecurity Inc. et al.

Written Opinion of the International Searching Authority of Internationai Patent Application PCT/CA2010/001200, Optosecurity Inc. et al.

International Search Report of International Patent Application PCT/CA2010/001200, Optosecurity Inc. et al.

Office Action mailed on Oct. 6, 2010 in connection with Canadian Patent Application 2,696,031—2 pages.

Office Action mailed on Oct. 29, 2010 in connection with Canadian Patent Application 2,651,728—6 pages.

Office Action mailed on Oct. 28, 2010 in connection with Canadian Patent Application 2,676,903—2 pages.

Office Action mailed on Nov. 2, 2010 in connection with Canadian Patent Application 2,690,163—1 pages.

Office Action mailed on Nov. 17, 2010 in connection with Canadian Patent Application 2,709,468—2 pages.

Examiner's Report mailed on Jan. 31, 2011 in connection with Canadian Patent Application 2,697,525—2 pages.

Office Action mailed on Feb. 9, 2011 in connection with U.S. Appl. No. 12/311,522—11 pages.

Office Action mailed on Feb. 8, 2011 in connection with U.S. Appl. No. 12/385,253—14 pages.

Office Action mailed on Mar. 2, 2011 in connection with U.S. Appl. No. 12/311,031—9 pages.

Examiner's Report mailed on Mar. 29, 2011 in connection with Canadian Patent Application 2,725,626—5 pages.

Examiner's Report mailed on Mar. 29, 2011 in connection with Canadian Patent Application 2,690,831—2 pages.

Hewei Gao, et al; "Application of X-ray CT to liquid security inspection: System analysis and beam hardening correction", Nuclear Instruments & Methods in Physics Research, Section-A: Accelerators; Spectrometers, Detectors and Associated Equipment, Elsevier, Amsterdam, NL, vol. 579, No. 1, pp. 395-399, Aug. 8, 2007.

Examiner;s Report mailed May 2, 2011 in connection with Canadian patent Appln. 2,692,662-3 pages.

European Search Report; mailed Jun. 9, 2011 EP Appln. No. EP2007815851.6-6 pages.

USPTO OA mailed Apr. 20, 2011 in connection with U.S. Appl. No. 12/311,031.

USPTO NOA mailed May 5, 2011 in connection with U.S. Appl. No. 12/385,253.

USPTO NOA mailed May 6, 2011 in connection with U.S. Appl. No. 12/311,522.

* cited by examiner

US 8,014,493 B2

METHOD AND DEVICES FOR ASSESSING THE THREAT STATUS OF AN ARTICLE AT A SECURITY CHECK POINT

CROSS-REFERENCE TO RELATED APPLICATIONS

This application claims the benefit under 35 USC §120 of:
U.S. provisional patent application Ser. No. 61/094,743 filed on Sep. 5, 2008 by Michel Roux et al.; and
U.S. provisional patent application Ser. No. 61/097,060 filed on Sep. 15, 2008 by Michel Roux et al.

This application also claims the benefit of priority under 35 USC §119 based on international PCT patent application no.: PCT/CA2007/001749 filed in the Canadian Receiving Office on Oct. 1, 2007 by Aidan Doyle et al. and presently pending.

The contents of the above-referenced patent documents are incorporated herein by reference.

FIELD OF THE INVENTION

The present invention relates to technologies for assessing the threat status of materials by means of penetrating radiation such as X-rays. The invention has numerous applications, in particular it can be used for scanning hand carried baggage at airport security check points.

BACKGROUND

Some liquid or combinations of liquid and other compounds may cause enough damage to bring down an aircraft. As no reliable technology-based solution currently exists to adequately address this threat, authorities have implemented a ban of most liquid, gels and aerosols in cabin baggage.

As a result, there have been disruptions in operations (e.g., a longer screening process; additional line-ups), major inconveniences for passengers (as well as potential health hazards for some) and economic concerns (e.g., increased screening costs; lost revenues for airlines and duty free shops; large quantities of confiscated—including hazardous—merchandise to dispose of), and so on.

Clearly, there is a need to provide a technology-based solution to address the threat of fluids that are flammable, explosive or commonly used as ingredients in explosive or incendiary devices.

SUMMARY

As embodied and broadly described herein the invention provides a method for performing security screening at a checkpoint. The method includes providing an X-ray imaging system having a scanning area and providing a supporting device for supporting articles to be scanned in the scanning area, wherein the supporting device has at least two reference areas manifesting respective X-ray signatures when exposed to X-rays, the X-ray signatures being distinguishable from one another. The method further includes placing an article to be scanned on the supporting device, introducing the article to be scanned in the scanning area while the article is supported by the supporting device and using the X-ray imaging system for deriving the X-ray signatures of the reference areas and for obtaining an X-ray image of the article while the supporting device is in the scanning area. Yet, the method includes using the X-ray signatures to derive X-ray attenuation information from the X-ray image and using the X-ray attenuation information in determining if the article is a security threat.

As embodied and broadly described herein the invention also includes a X-ray inspection station for performing security screening on articles, the X-ray inspection station having an X-ray scanning area where one or more articles are exposed to X-rays and a supporting device for supporting one or more articles while the articles are exposed to X-rays in the scanning area, wherein the supporting device has at least two reference areas manifesting respective X-ray signatures when exposed to X-rays, the X-ray signatures being distinguishable from one another. A computer based processing unit is provided for:
  i) deriving the X-ray signatures of the reference areas and collecting X-ray image data of the article while the supporting device is in the scanning area;
  ii) using the X-ray signatures to derive X-ray attenuation information from the X-ray image data;
  iii) using the X-ray attenuation information in determining if the article is a security threat.

As embodied and broadly described herein the invention also includes a tray for supporting an article while the article is subjected to an X-ray inspection in an X-ray imaging apparatus, the X-ray imaging apparatus including an array of X-ray detectors, the tray including at least two reference areas manifesting respective X-ray signatures that are distinguishable from one another, at least one of the reference areas having an extent such that X-rays passing through the reference area are received by a majority of the X-ray detectors of the array of X-ray detectors.

As embodied and broadly described herein the invention also includes a belt for carrying an article to be subjected to an X-ray inspection in and out of the scanning area of an X-ray imaging apparatus, the belt including at least two reference areas manifesting respective X-ray signatures when exposed to X-rays, the X-ray signatures being distinguishable from one another.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

A detailed description of examples of implementation of the present invention is provided herein below with reference to the following drawings, in which.

Figure 1:
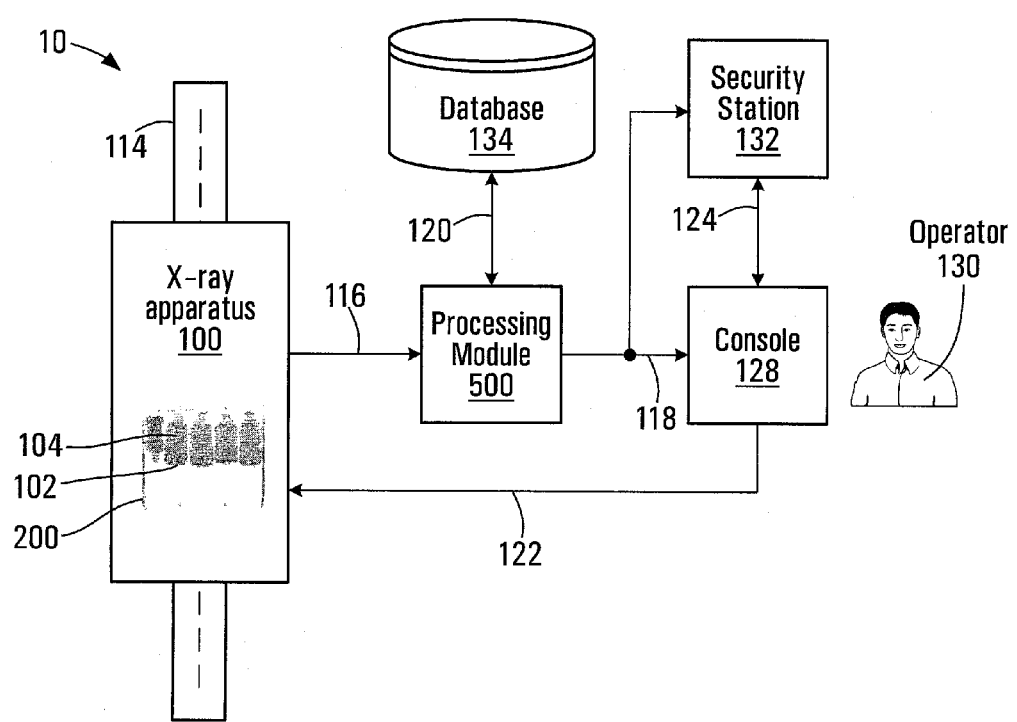
FIG. 1 is a block diagram of an apparatus using X-rays to scan hand carried baggage at a security check point, according to a non-limiting example of implementation of the invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

With reference to FIG. 1, there is shown a specific non-limiting example of a system 10 for use in screening containers with liquids, in accordance with a non-limiting embodiment of the present invention. The system 10 comprises an X-ray imaging apparatus 100 that applies an X-ray screening process to a material such as a liquid 104 contained in a container 102 that is located within a screening area of the X-ray imaging apparatus 100. In an airport setting, a passenger may place the container 102 in a tray which is then placed onto a conveyor 114 that causes the container 102 to enter the screening area of the X-ray imaging apparatus 100. The X-ray imaging apparatus 100 outputs an image signal 116 to a processing module 500. The processing module then processes the X-ray image data conveyed by the signal 116.

The processing module 500 may be co-located with the X-ray imaging apparatus 100 or it may be remote from the X-ray imaging apparatus 100 and connected thereto by a communication link, which may be wireless, wired, optical, etc. The processing module 500 processes the image data and executes a method to produce a threat assessment 118. The processing module 500 is computer based and its functionality is provided by suitable software executing on a computing platform.

The threat assessment 118 is provided to a console 128 and/or to a security station 132, where the threat assessment 118 can be conveyed to an operator 130 or other security personnel. The console 128 can be embodied as a piece of equipment that is in proximity to the X-ray imaging apparatus 100, while the security station 132 can be embodied as a piece of equipment that is remote from the X-ray imaging apparatus 100. The console 128 may be connected to the security station 132 via a communication link 124 that may traverse a data network (not shown).

The console 128 and/or the security station 132 may comprise suitable software and/or hardware and/or control logic to implement a graphical user interface (GUI) for permitting interaction with the operator 130. Consequently, the console 128 and/or the security station 132 may provide a control link 122 to the X-ray imaging apparatus 100, thereby allowing the operator 130 to control motion (e.g., forward/backward and speed) of the conveyor 114 and, as a result, to control the position of the container 102 within the screening area of the X-ray imaging apparatus 100.

In accordance with a specific non-limiting embodiment the X-ray imaging apparatus 100 is a dual-energy X-ray imaging apparatus 100. However, persons skilled in the art will appreciate that the present invention is not limited to such an embodiment. Such dual-energy X-ray imaging apparatus 100 has a source which emits X-rays at two distinct photon energy levels, either simultaneously or in sequence. Example energy levels include 50 keV (50 thousand electron-volts) and 150 keV, although persons skilled in the art will appreciate that other energy levels are possible.

The processing module 500 receives the image signal 116 and processes the signal to determine if the liquid 104 in the container 102 poses a security threat. The determination can include an explicit assessment as to weather the liquid 104 is a threat or not a threat. Alternatively, the determination can be an identification of the liquid 104 or the class of materials to which the liquid 104 belongs, without explicitly saying whether the liquid 104 is threatening or not threatening. For example, the processing module can determine that the liquid 104 is "water" hence the operator 130 would conclude that it is safe. In a different example, the processing module 500 determines that the liquid 104 belongs to a class of flammable materials, in which case the operator 130 would conclude that it would be a security threat. Also, the determination can be such as to provide an explicit threat assessment and at the same time also provide an identification of the liquid 104 in terms of general class of materials or in terms of a specific material. The results of the determination are conveyed in the threat assessment signal 118 which is communicated to the console 128 and/or the security station 132 where it is conveyed to the operator 130.

Figure 4:
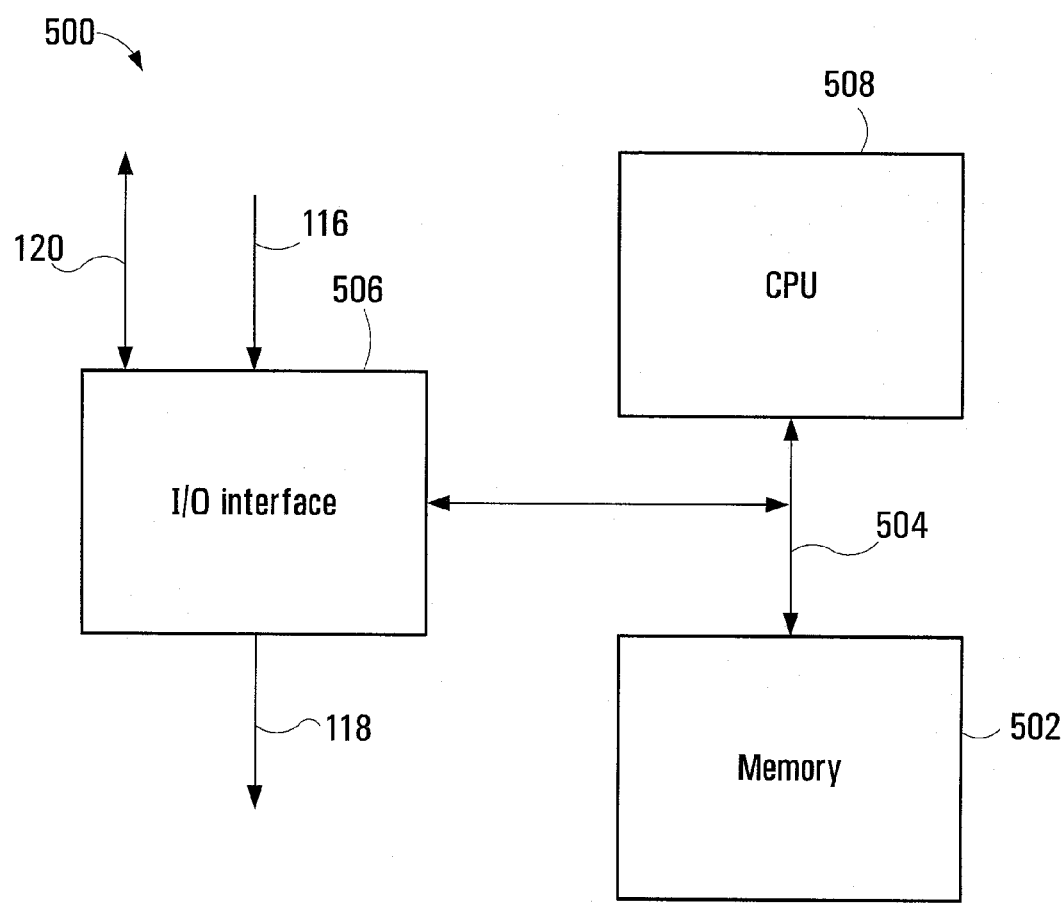
FIG. 4 is a block diagram of the processing module of the apparatus shown in FIG. 1.

FIG. 4 is a high level block diagram of the processing module 500. The processing module 500 has a Central Processing Unit (CPU) 508 that communicates with a memory 502 over a data bus 504. The memory 502 stores the software that is executed by the CPU 508 and which defines the functionality of the processing module 500. The CPU 120 exchanges data with external devices through an Input/Output (I/O) interface 506. Specifically, the image signal 116 is received at the I/O interface 506 and the data contained in the signal is processed by the CPU 508. The threat assessment signal 118 that is generated by the CPU 508 is output to the console 128 and/or the security station 132 via the I/O interface 506.

Figure 2:
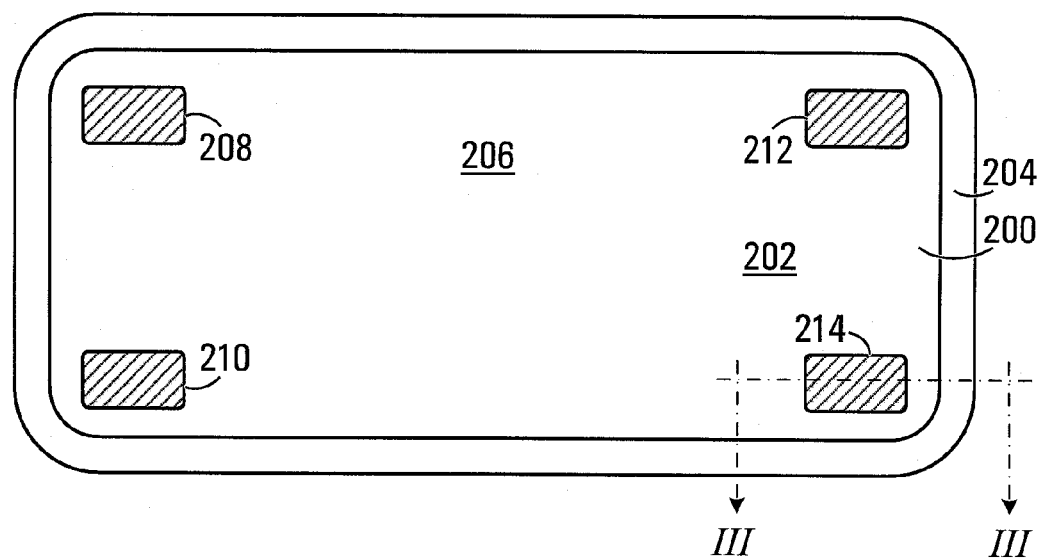
FIG. 2 is a plan view of a tray for carrying materials as they undergo security screening, according to a non-limiting example of implementation of the invention.

In a specific example of implementation, the system 10 is used in conjunction with a tray 200 shown in FIG. 2 to perform security screening of liquid products. The tray 200 is used as a receptacle in which objects to be screened, such as liquid products or other materials or articles, are placed and put on the conveyor belt of the X-ray imaging system 100. The tray 200 is provided with one or more distinct areas that have X-ray signatures which can be used as references against which the X-ray imaging apparatus 100 can self-calibrate.

The tray 200 defines a surface 202 which is generally flat and on which the liquid product that is being screened rests. In the example shown in the drawings, the surface is shaped as a rectangle with rounded corners. Evidently, different shapes or configurations can be used without departing from the spirit of the invention.

The surface 202 is provided with raised edges or rim 204 that extend in a continuous fashion around the periphery of the surface 202. The raised edges 204 prevent articles placed in the tray 200 to fall outside during the screening operation.

The height of the raised edges 204 can vary without departing from the spirit of the invention.

The surface 202 defines five distinct areas. The first area 206 is the base material from which the tray 200 is made. That material may be any synthetic material that has the required strength and durability characteristics for the intended application. The four additional distinct areas 208, 210, 212 and 214 are in the form of inserts that are placed in respective receptacles in the base material 206. The areas 208, 210, 212 and 214 are in the shape of rectangles placed near respective corners of the tray 200. It is to be expressly noted that the shape, placement in the tray 200 and the number of the areas 208, 210, 212 and 214 can vary without departing from the spirit of the invention.

The areas 206, 208, 210, 212 and 214 are distinct in that they have different X-ray signatures. Accordingly, when an X-ray image is taken of the tray 200 alone, the areas 206, 208, 210, 212 and 214 will show up differently in the image. Preferably, the area 206 is made of material that is selected to provide a weak X-ray signature such as to limit its effect in the image and thus make the other articles that are put on the tray 200 more visible. In that sense, the area 206 attenuates the X-ray beam little or not at all. In contrast, the areas 208, 210, 212 and 214 are designed to provide different levels of X-ray attenuation, as it will be discussed later.

Figure 3:
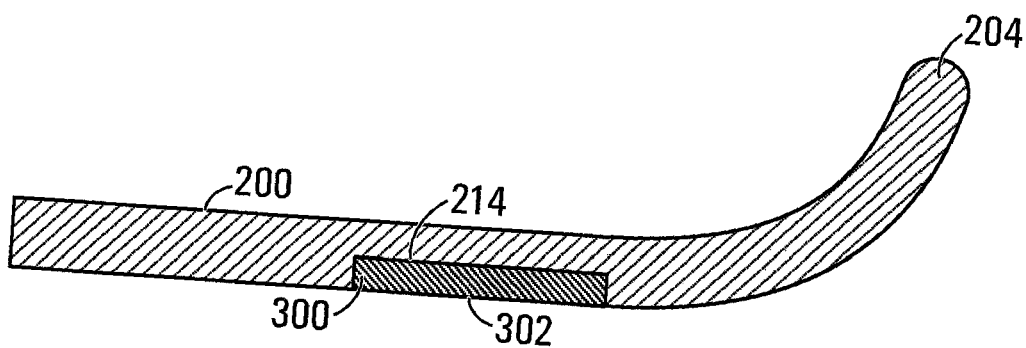
FIG. 3 is a cross-sectional view taken along lines 3-3 in FIG. 2.

More specifically, each area 208, 210, 212 and 214 can be made from a material providing the desired degree of X-ray attenuation. This solution can be implemented by providing an insert made from the selected material that is placed in the base material 206 of the tray 200. This feature is best shown in FIG. 3 which is a cross-sectional view of the tray 200 taken at the level of the area 214. Specifically, the base material of the tray is provided with a receptacle 300 in which is placed an insert 302 defining the area 214. To ensure a snug fit the insert 302 is manufactured to be of about the same size as the receptacle 300. In this fashion, the insert 302 is held in the receptacle 300 as a result of friction fit. Evidently, other mounting methods can be provided without departing from the spirit of the invention. One possible variant is to use a fastening mechanism that would allow the insert 302 to be removed. In this fashion, the insert 302 can be replaced with another insert, if the original insert is damaged or if it is deemed appropriate to change the X-ray signature of the area 214.

In a specific and non-limiting example of implementation the X-ray signature of anyone of the reference areas 206, 208, 210, 212 and 214 can be expressed as the gray scale level intensity of the pixels in the portion of the X-ray image that depicts respective reference area. Generally, the gray scale level intensity represents the degree of attenuation of the X-rays as they pass through the object. The grey scale level can be relatively uniform across the reference area 206, 208, 210, 212 and 214. This is the case when the reference area 206, 208, 210, 212 and 214 is made of material that is homogenous and thus attenuates X-rays uniformly. Another example of an X-ray signature is a situation when the area 206, 208, 210, 212 and 214 is not homogeneous and thus creates a certain gray scale level profile or pattern. The pattern may be regular or irregular.

Generally speaking, the X-ray signature of a reference area 206, 208, 210, 212 and 214 is the response produced by the reference area 206, 208, 210, 212 and 214 when the reference area 206, 208, 210, 212 and 214 interacts with X-rays. There are a number of interactions possible, such as:

The Rayleigh scattering (coherent scattering)
The photoelectric absorption
The Compton scattering (incoherent scattering)
The pair production
Diffraction The photoelectric absorption of X-rays occurs when an X-ray photon is absorbed, resulting in the ejection of electrons from the shells of the atom, and hence the ionization of the atom. Subsequently, the ionized atom returns to the neutral state with the emission of whether an Auger electron or an X-ray characteristic of the atom. This subsequent X-ray emission of lower energy photons is however generally absorbed and does not contribute to (or hinder) the X-ray image making process. This type of X-ray interaction is dependent on the effective atomic number of the material or atom and is dominant for atoms of high atomic numbers. Photoelectron absorption is the dominant process for X-ray absorption up to energies of about 25 keV. Nevertheless, in the energy range of interest for security applications (for today's state-of-the-art security screening systems, the energy levels commonly utilized lie between 50 keV and 150 keV), the photoelectric effect plays a smaller role for low Zeff values with respect to the Compton scattering, which becomes dominant.

Compton scattering occurs when the incident X-ray photon is deflected from its original path by an interaction with an electron. The electron gains energy and is ejected from its orbital position. The X-ray photon looses energy due to the interaction but continues to travel through the material along an altered path. Since the scattered X-ray photon has less energy, consequently it has a longer wavelength than the incident photon. The event is also known as incoherent scattering because the photon energy change resulting from an interaction is not always orderly and consistent. The energy shift depends on the angle of scattering and not on the nature of the scattering medium. Compton scattering is proportional to material density and the probability of it occurring increases as the incident photon energy increases.

The diffraction phenomenon of the X-rays by a material with which they interact is related to the scattering effect described earlier. When the X-rays are scattered by the individual atoms of the material, the scattered X-rays may then interact and produce diffraction patterns that depend upon the internal structure of the material that is being examined.

As to the pair production interaction, it refers to the creation of an elementary particle and its antiparticle from an X-ray photon.

That response produced by a material as it interacts with X-rays can be expressed in terms of gray level value, gray level patterns seen in the X-ray image or other physical manifestation.

The selection of the proper material for making the inserts 302 for the various reference areas 208, 210, 212 and 214 can be made by in a number of ways. The insert may or may not be made from a homogenous material. An example of a non-homogeneous structure is an assembly of layers made from different materials that in combination would provide the desired X-ray signature. Another example is a mixture of different materials intended to create a pattern in the X-ray image. The person skilled in the art will recognize that an almost infinite number of different X-ray signatures can be developed by selecting the proper material or materials and by mixing or assembling them in the appropriate manner.

Examples of materials that can be used include plastics such as polyethylene, polypropylene or others. Their density or composition can be varied to obtain the desired X-ray signature.

An advantage of performing a comparison between X-ray signatures extracted from the same image data is the elimination or at least the reduction of X-ray induced variations in the system response. In this fashion, the system is self-referencing.

Figure 5:
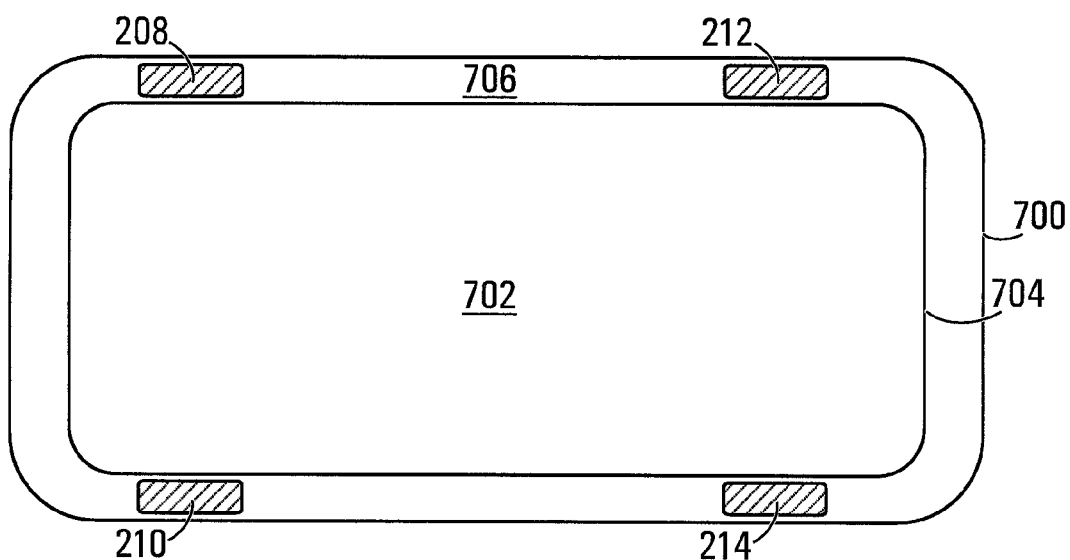
FIG. 5 is a plan view of the tray according to a variant.

The example of implementation shown in FIG. 2 depicts the areas 208, 210, 212 and 214 placed in the respective corners of the tray 200. This is done in order to reduce the likelihood of obscuring anyone of those areas 208, 210, 212 and 214 by an article that is placed in the tray. For instance, if an article is put in the tray immediately above anyone of those areas 208, 210, 212 and 214, the X-ray signature of that area may not be correctly read since the X-ray image will be the result of a composite response (the area 208, 210, 212 and 214 and the article on top of it). In order to further reduce the possibility of obscuring the areas 208, 210, 212 and 214 it is possible to place the areas 208, 210, 212 and 214 at a location that is outside the zone in the tray where the articles to be screened are located. An example of such embodiment is shown in FIG. 5. The tray 700 defines a central article receiving area 702 in which are placed the articles to be screened. The article receiving area 702 is surrounded by a rim portion 704 that extends peripherally and fully encircles the article receiving area 702. The rim portion 704 has a top area 706 that is flat and that is sufficiently wide such as to accept the reference areas 208, 210, 212 and 214. In this fashion, articles to be screened are unlikely obscure anyone of the areas 208, 210, 212 and 214 that remain outside the central article receiving area.

The tray 200 provides a material reference during the X-ray scanning process which can be used to limit or avoid altogether machine induced variations in the results by performing a self-calibration operation. Since in practice different X-ray imaging apparatuses are never identical and manifest some variations that can be either at the level of the X-ray detectors elsewhere in the machine, those variations can impact the detection results.

More specifically, the tray 200 can be used as a known reference for the X-ray imaging apparatus 10. Accordingly, when the X-ray scanning process is performed the X-ray imaging apparatus 100 can use the X-ray signature of the tray 200 to self-calibrate.

Since in the course of an X-ray scanning operation the tray 200 will be used repeatedly, the self-calibration operation occurs with regularity, thus enhancing the performance of the X-ray imaging apparatus in terms accuracy in identifying security threats.

Figure 6:
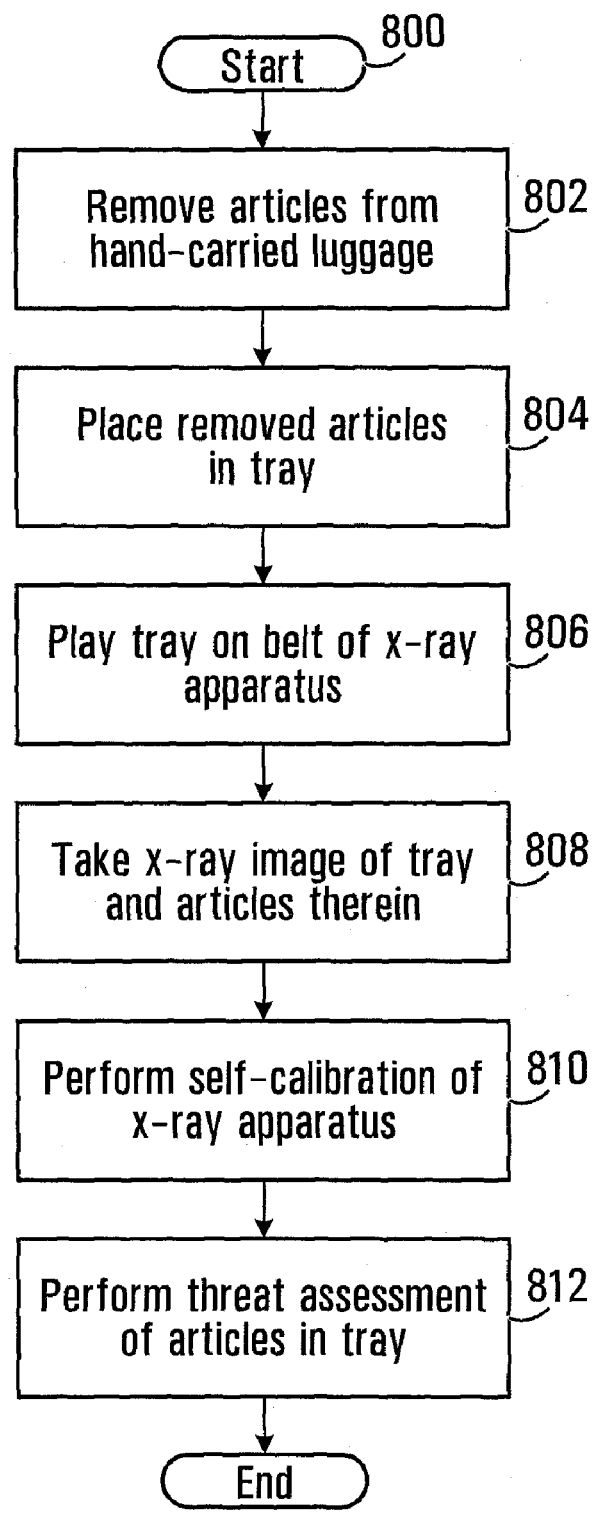
FIG. 6 is a flow chart of a process according to a non-limiting example of the invention for performing threat assessment.

A general view of the threat assessment and self-calibration process is shown at FIG. 6. At step 800 the process starts. At step 802 a passenger at a security checkpoint, such as at an airport, removes articles from his/her hand carried luggage. Examples of articles include containers holding liquids or other articles such as electronic equipment.

At step 804 the removed articles are placed in a tray that includes reference areas, say tray 700. In addition to the articles that are removed from the hand carried luggage, additional articles can also be included such as shoes (in the instance the individual is being requested by security personnel to have his/her shoes scanned), a belt and a jacket among others.

At step 806 the tray 700 is placed on the belt 114 of the X-ray imaging apparatus 100, which carries the tray 700 with the articles therein inside the X-ray imaging apparatus 100.

At step 808 an x-ray image of the tray 700 and of the articles therein is taken. The X-ray image data is then processed at step 810 to perform a self-calibration of the X-ray imaging apparatus 100. Once the X-ray imaging apparatus 100 is self-calibrated, the x-ray image data is processed to perform a threat assessment of the articles in the tray 700.

In this example, the self-calibration of the X-ray imaging apparatus 100 and the threat status assessment are performed during the same X-ray scanning cycle. This self-calibration can be repeated at every scanning cycle, thus reducing as much as possible machine induced variations over time. If machine induced variations drift over time, such as the result of temperature, humidity of other environmental factors, the repeated self-calibration will track those drifts and thus enhance the detection results.

Once the scanning operation is completed the person takes away his/her belongings from the tray. The empty tray is then brought back and placed near the entry side of the X-ray imaging apparatus such that it can be used by another person. If every tray in the set of trays provided with the X-ray imaging apparatus 100 use reference areas, every time a tray is used to perform a scan of articles, a self-calibration operation occurs.

Note that it is not essential to perform self-calibration every time the X-ray imaging apparatus 100 scans articles to detect their threat status. One possibility is to perform the self-calibration operation at every other scanning cycle or at any other frequency deemed appropriate for the intended application. The selection of the frequency at which the self-calibration will occur can be done in a number of possible ways, namely:

1. The set of trays that are used to scan articles in the X-ray imaging apparatus 100 is provided with a sub-set that enable the self-calibration (trays with reference areas) and a sub-set that cannot be used to perform self-calibration (trays without any reference areas). Since those trays are used repeatedly, the self-calibration process will occur only when a tray with reference areas is being scanned. The frequency at which the self-calibration occurs can be set by determining the mix of trays that enable self-calibration and those that do not, as desired.
2. The X-ray imaging apparatus 100 can be programmed such as to run the self-calibration process for one tray in a sequence of trays that are being scanned, such as every second, third or fourth tray, for instance.
3. The X-ray imaging apparatus can be manually controlled to run the self-calibration. The X-ray imaging apparatus has on its console 300 controls that are actuated by the operator to run the self-calibration. The operator thus takes the decision at which frequency the self-calibration occurs.

The self-calibration operation, in terms of X-ray image data processing will be described in greater detail in connection with FIGS. 7, 8 and 9.

Figure 7:
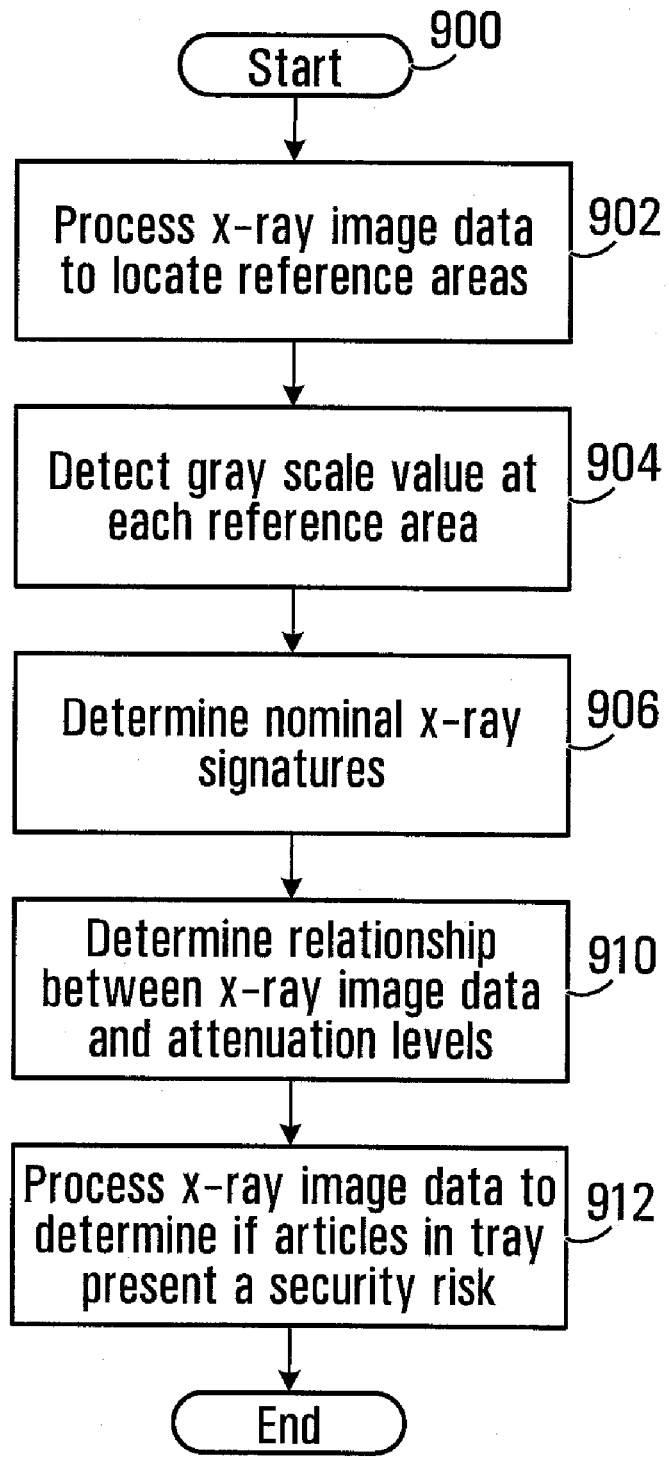
FIG. 7 is a flow chart of a process according to a non-limiting example of the invention for performing self-calibration of the X-ray imaging apparatus of FIG. 1.

With reference to FIG. 7, the process starts at step 900. At step 902 the X-ray image data is processed by the processing module 200 to locate the reference areas in the tray. At step 904 the X-ray signature of each reference area is acquired. In the example shown in the drawing, the X-ray signature is conveyed by the grey scale level or value of the reference area in the image. Accordingly, the grey scale value associated with each reference area is measured to acquire the X-ray signature.

Figure 8:
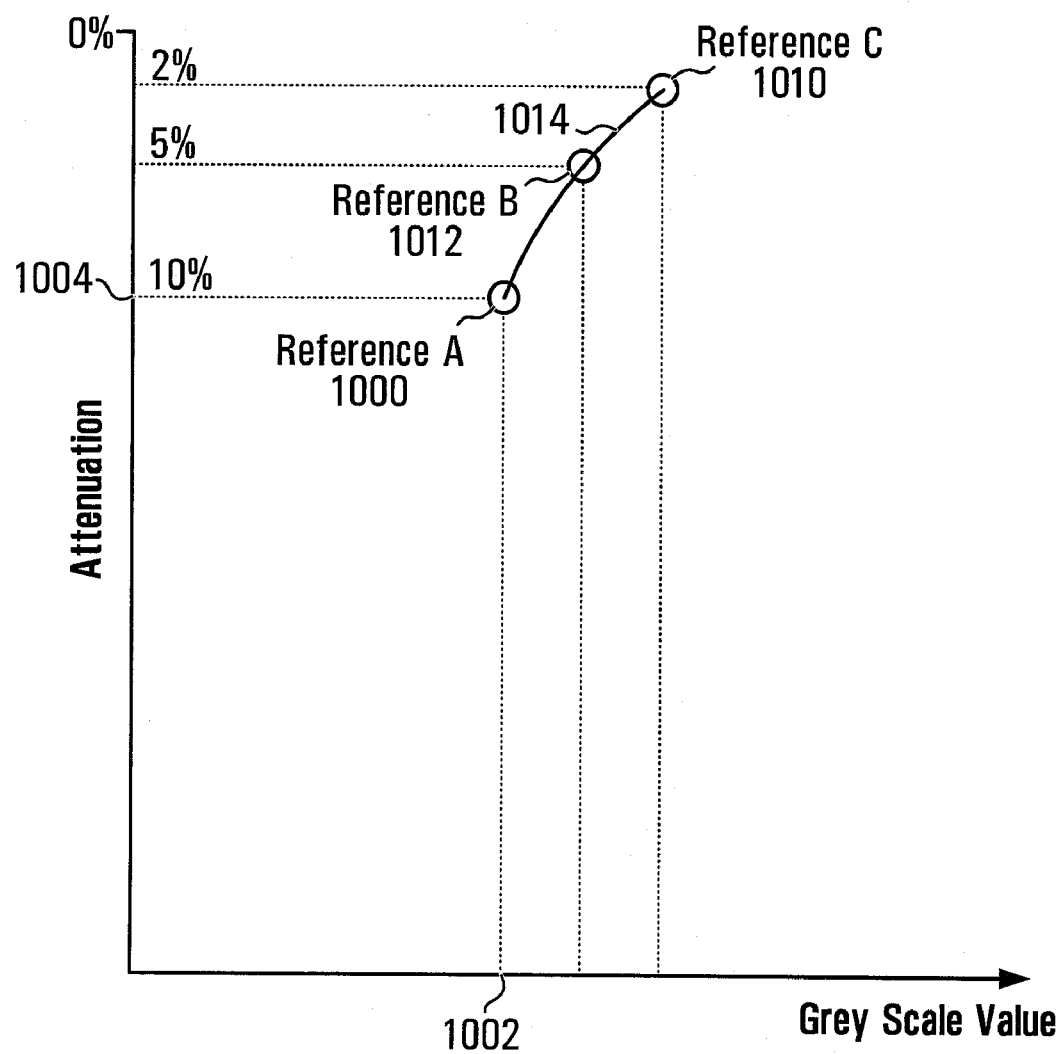
FIG. 8 is a graph illustrating the relationship between grey scale values in an X-ray image and corresponding attenuation levels.

As can be seen in the graph at FIG. 8, each grey scale value can be mapped to a certain X-ray attenuation level. At step 906 the nominal X-ray signatures of the respective reference areas are obtained. In this specific example, the nominal X-ray signatures are associated with specific attenuation information. The nominal X-ray signatures can be obtained from different sources, as generally described earlier. For instance, the nominal X-ray signatures are stored in a database that is accessible to the processing module 200. By performing the analysis of the X-ray image data, the processing module 200 can extract the identities of the reference areas and on the basis of the identity information extract the signature information from the database. Alternatively, the nominal X-ray signatures can be encoded directly in the tray such that they can be read by the processing module in the X-ray image data. One example is a bar-code encoding that is machine readable.

At step 910 nominal X-ray signatures are used by the processing module 200 to create a relationship between the X-ray image data and corresponding attenuation information. This is best illustrated in the graph of FIG. 8 which maps grey scale values to attenuation levels. The process is performed by software executed by the processing module 200.

Assume that the tray has three different reference areas, namely reference area A, a reference area C and an intermediate reference area B. Reference areas A, B and C are associated with progressively decreasing attenuation levels. For the sake of this example, consider that reference area A is associated with a 10% attenuation level, reference area B with 5% attenuation level and reference area C with 2% attenuation level.

The grey scale value associated with the reference area A is plotted against an attenuation values axis (at the known 10% attenuation level) to create a data point 1000.

The grey scale value 1006 associated with the reference C is also plotted against the attenuation values axis at the known value of 5%, which creates a second data point 1010.

The data points 1000 and 1010 can be used to establishing a linear relationship between the X-ray image data and corresponding attenuation levels, where the relationship is corrected with respect to known references (A and C). Note that in this example, the X-ray image data is expressed in terms of grey scale values and the relationship is therefore established between the grey scale values read from the image and the attenuation levels. However, in situations where the X-ray image data is conveyed in a way other than grey scale values, the data conveying the image information can equally well be mapped to attenuation levels.

The two data points 1000 and 1010 allow creating a linear relationship between the grey scale values and the attenuation levels. In this fashion, any grey scale values residing between the grey scale values of data points 1000 and 1010 will be mapped to attenuation levels according to a linear relation. In practice, this linear relationship may not accurately reflect the reality of the physics involved, in which case additional data points can be used to create a more accurate map. In the example shown in FIG. 10, the intermediate reference B provides a data point 1012 that corresponds to 5% attenuation. An algorithm can be used to create a best fit curve over the three data points which will define the relationship between the grey scale values and the attenuation levels.

While the above example illustrates a situation where the reference areas A, B and C are all located in the lower end of the attenuation level scale, in the range between 2% and 10%, the references can be selected in a different area of the scale. More particularly, the references can be selected such as to cover a wider range of attenuations, a range of attenuations located near the upper end of the attenuation level scale (close to 100% attenuation), or anywhere else between the upper end and the lower end. For instance, in a variant, the references can be selected such as to span the entire scale.

From the point of view of calibration results, the location of the reference areas in the lower end of the attenuation scale (low attenuation) allows calibrating the X-ray imaging apparatus 10 in the operating range where the apparatus usually manifests the most drift. Accordingly, performing a calibration in this area is likely to improve in a tangible way the accuracy of detection.

Figure 15:
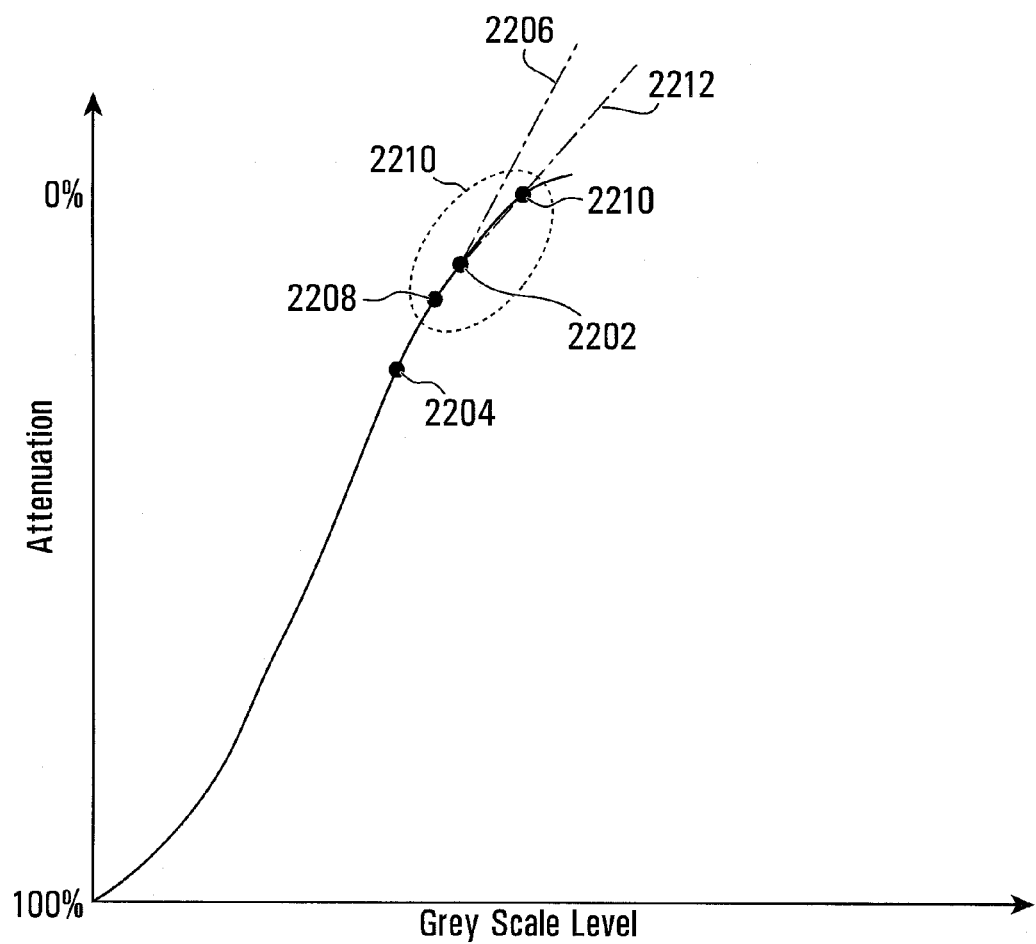
FIG. 15 is a graph showing the relationship between the grey scale level in X-ray image data and attenuation values.

In addition, the lower end of the attenuation scale (low attenuation) tends to be non-linear; accordingly the placement of reference areas in that region is likely to produce a more accurate map between the grey scale levels and the corresponding attenuation values. FIG. 15 illustrates this point. FIG. 15 shows a graph of the relationship between the grey scale levels and attenuation over the entire attenuation range, namely 0% to 100%. The region 2200, in the lower end of the attenuation scale (low attenuation) is non-linear. In a scenario where two reference points are used for the calibration and they are placed such as to locate one (point 2202) in the region 2200 and one (point 2204) outside the region 2200, the resulting map 2206 may not track well the curve. In a different scenario, where the reference points 2208 and 2210 are all placed in the region 2200, the resulting map 2212 better follows the curve.

Figure 9:
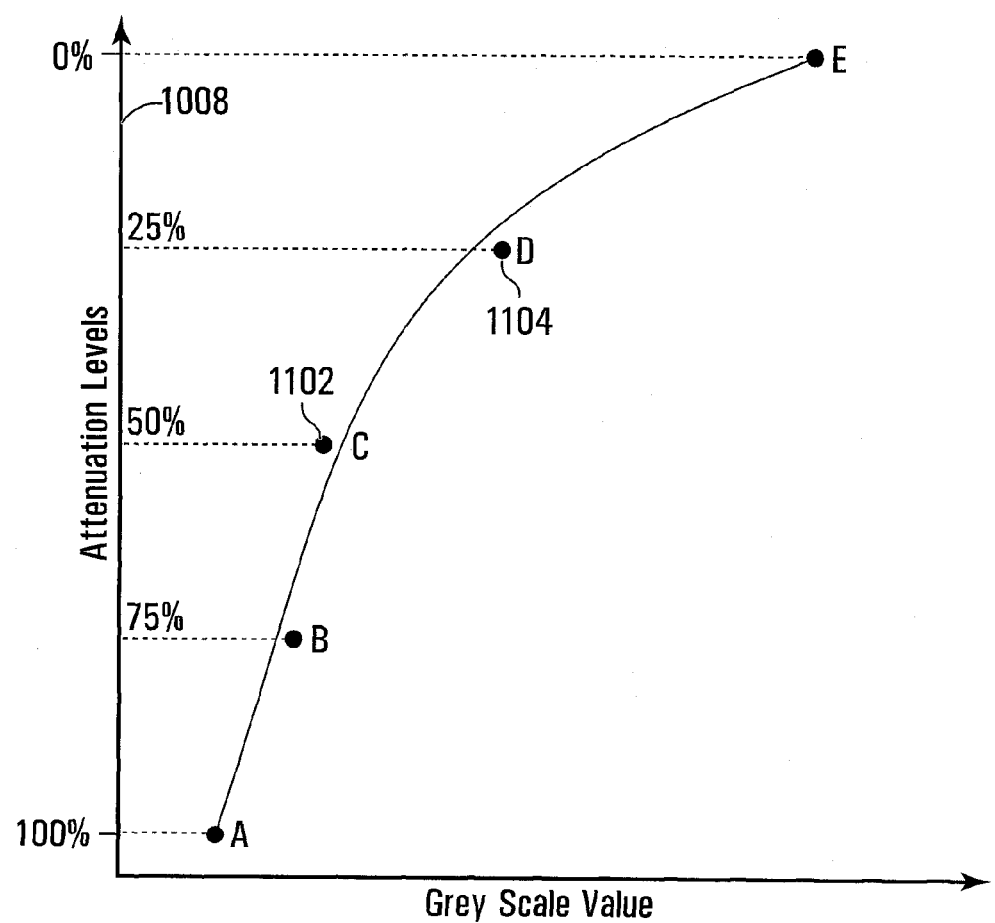
FIG. 9 is another graph illustrating the relationship between grey scale values in an X-ray image and corresponding attenuation levels.

FIG. 9 provides an example of a different situation where the tray has 5 reference areas spread over the entire attenuation range, namely reference areas D, E, F, G and H corresponding to 100%, 75%, 50% and 25% attenuation levels, respectively. By using a best fit algorithm a curve can be laid over the data points that establish the relationship between the grey scale values and the attenuation levels.

Referring back to FIG. 7, the process terminates at step 912 by analyzing the X-ray image data to determine if the articles in the tray present a security threat. To perform the threat assessment the processing module 200 determines the levels of X-ray attenuation associated to pixels or groups of pixels in the X-ray image. The level of attenuation is obtained on the basis of the relationship established earlier where grey-scale values are mapped to attenuation levels, and the resulting map is stored in the memory of the processing module 200. The processing module 200 uses the grey scale level as an input to the attenuation map and derives an attenuation values, accordingly. The attenuation values are then processed to determine the threat status of the articles.

Figure 11:
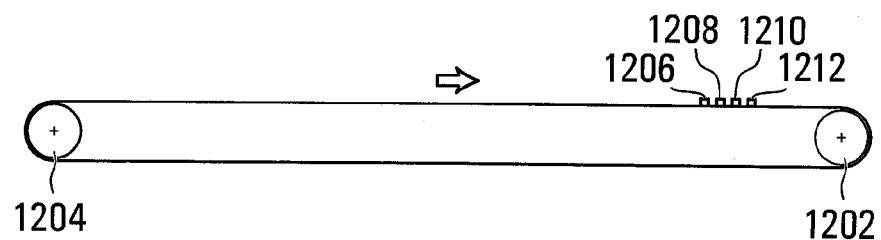
FIG. 11 is a side elevation view of the belt shown in FIG. 10.
Figure 12:
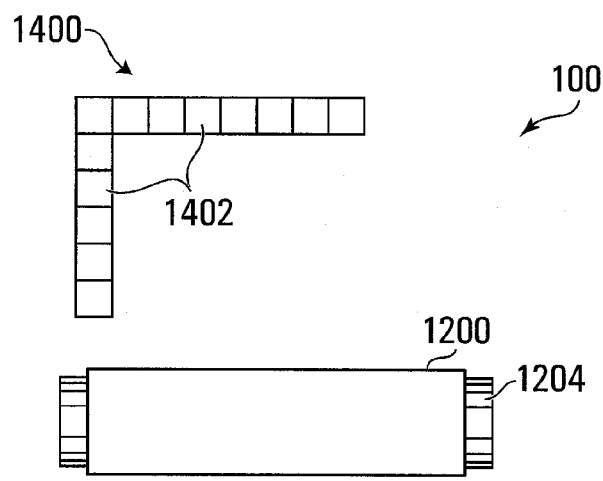
FIG. 12 is a front elevation view of the belt of FIGS. 10 and 11, also showing the detectors array of the X-ray imaging apparatus.

In a possible variant, the reference areas used to perform the self-calibration operation are associated with the belt 114 that is used to carry the tray and the articles to be scanned through the X-ray imaging apparatus 100. This example is best shown in FIGS. 10, 11 and 12.

Figure 10:
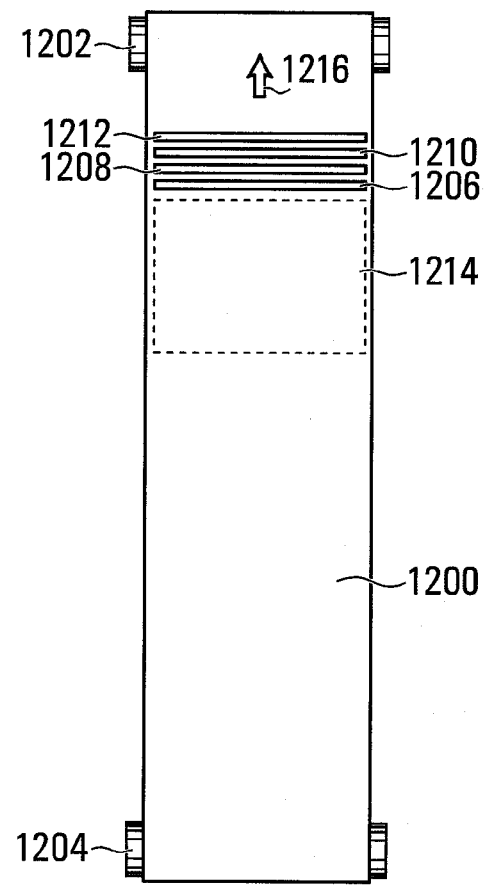
FIG. 10 is a top plan view of a belt of an X-ray imaging apparatus of the type shown in FIG. 1, the X-ray imaging apparatus being omitted for clarity.

FIG. 10 is a plan view of the belt 1200. The belt is an endless sheet mounted on two rollers 1202 and 1204. One or both of the rollers can be used to drive the belt such that it advances articles through the scanning station of the X-ray imaging apparatus 100'. The belt 1200 is provided with a plurality of reference areas. More specifically, four reference areas are used, namely reference areas 1206, 1208, 1210 and 1212. Each reference area is shaped as a strip of material that extends across the direction of movement of the belt 1200. In a specific example, the strips are oriented generally transversally with relation to the direction of movement of the belt 1200. The length of each reference area 1206, 1208, 1210 and 1212 is somewhat less than the transverse dimension of the belt 1200.

The materials that constitute the reference areas 1206, 1208, 1210 and 1212 can be mounted on top of the belt 1200 surface and secured thereto in any suitable fashion. Alternatively, the materials can be mounted on the bottom of the surface or imbedded in the belt 1200 such that they are not visible to the eye.

In operation the articles to be scanned (with or without tray) should not be placed directly over the reference areas 1206, 1208, 1210 and 1212 to avoid obscuring them. It is better if the articles to be scanned are immediately adjacent the reference areas 1206, 1208, 1210 and 1212 such that they do not overlap while at the same time the X-ray image data encompasses them both. To avoid an overlap an arrangement can be provided to indicate to the user that articles should not be placed over the reference areas 1206, 1208, 1210 and 1212. The arrangement can include a physical barrier, such projections (not shown extending outwardly of the belt 1200 surface which intuitively indicate that no articles can be placed at location on the belt. Alternatively, the arrangement includes markings to indicate to a user that no articles should be placed in that area. The markings my include text, pictograms or a combination of both.

Note that the markings can be used in conjunction with the physical barrier.

Yet the arrangement can also include markings to indicate where articles, including a tray, can be placed such as not to overlap with the reference areas. Those markings may be lines that delineate a boundary in which articles are to be placed. For instance, the marking may be in the shape of a rectangle 1214 indicating where articles to be scanned should be placed.

One advantage in using elongated strips of material to form the reference areas which are fed transversally to the direction of movement of the belt 1200 (the direction of movement is depicted by the arrow 1216) is to allow a majority of the X-ray detectors and preferably all of the X-ray detectors of the X-ray imaging apparatus 100 to sense the reference areas.

With specific reference to FIG. 12, which is a front view of the X-ray imaging apparatus 100, specifically showing the belt 1200 and a detector array 1400. The detector array 1400 has a plurality of detectors 1402 that are arranged to form an L-shape, including a horizontal arm and a vertical arm. The elongated strip of material can therefore be "seen" by each detector, which allows constructing for each detector an individual attenuation map of the type described earlier.

Figure 13:
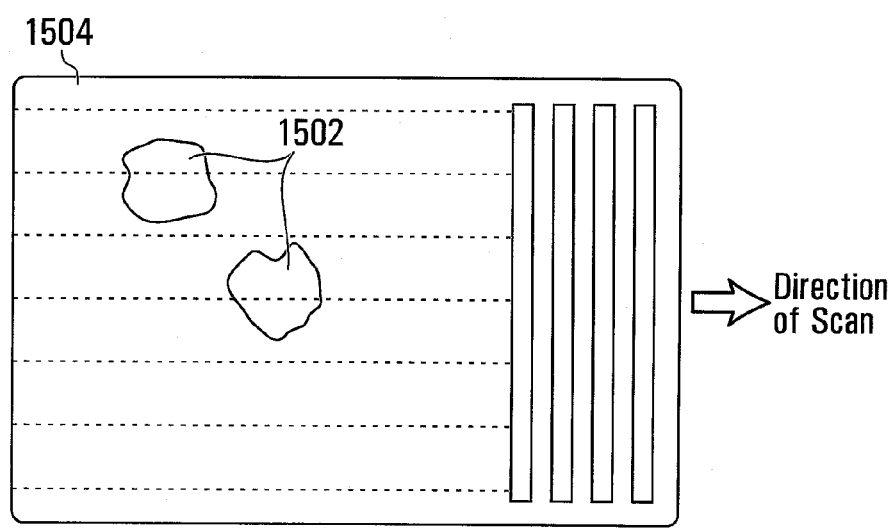
FIG. 13 is an example of an X-ray image, showing various image segments and how they relate to respective detectors of the detectors array.

This is best shown in FIG. 13 which is a representation of an X-ray image obtained from the detector array 1400. The image 1500 shows articles 1502 that are being scanned and also the reference areas. The X-ray image is assembled from individual image strips 1504, where each image strip is derived from the output of a detector 1402. Since the reference materials have geometry such that a portion of each of them appears in each image strip, that image strip can be processed independently to create a detector specific attenuation map.

Accordingly, the processing module 500 would therefore store in its memory a series of attenuation maps, one for each detector. In such case, when the X-ray image data is processed, the portions of the image data that are derived from a given detector are processed against the attenuation map of that detector to determine the attenuation values. For instance, grey scale levels of pixels in any one of the strips 1504 are used as inputs to the attenuation map of the detector associated with the image strip to determine the attenuation levels.

Figure 14:
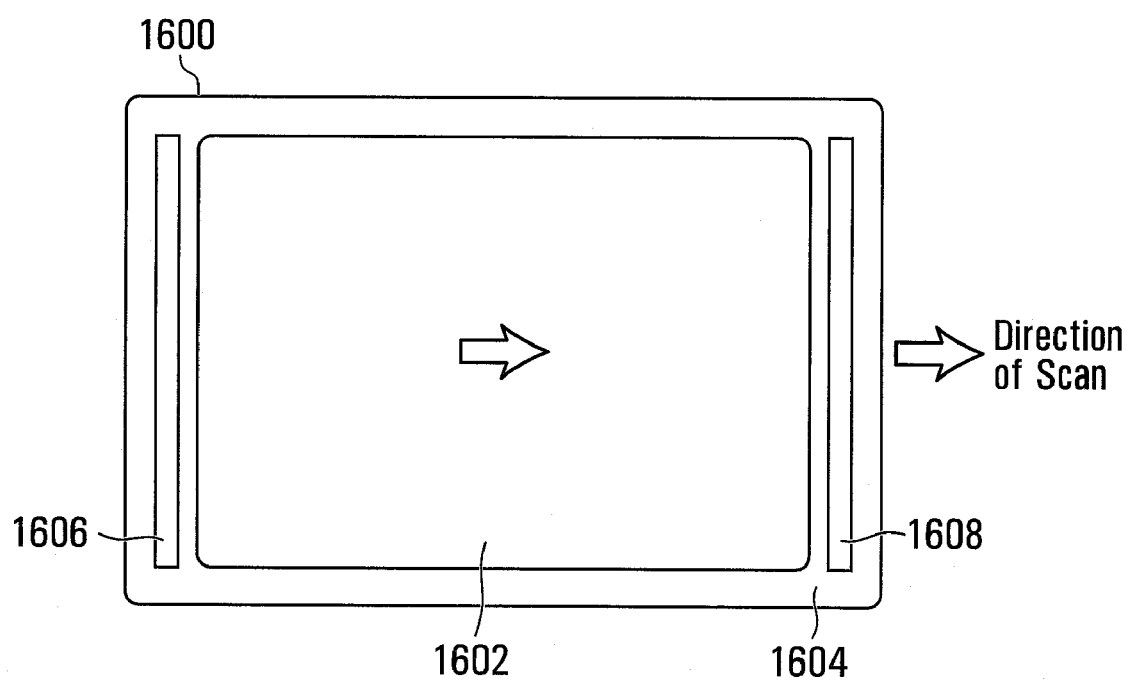
FIG. 14 is a top plan view of the tray according to a second variant.

Note that similar reference material geometries can be used on trays as well. FIG. 14 is a top plan view of a tray 1600 having an area 1602 to receive articles to be scanned and a rim portion 1604 on which are placed reference materials to form reference areas 1606 and 1608. In the example shown the tray 1600 is provided with two reference areas 1606 and 1608 but more can be provided if desired.

The tray has an imaginary longitudinal axis and an imaginary transverse axis. In use, the tray should be placed such that the reference areas 1606 and 1608 extend across the longitudinal axis, which coincides with the direction of movement of the tray in the scanning area of the X-ray imaging apparatus 10. In a specific example, the reference areas 1606 and 1608 are perpendicular to the direction of movement of the belt (arrow 1608). Markings can be placed on the tray such that users can place the tray in the proper orientation. The markings can include pictograms of text. An arrow placed on the bottom of the area 1602 is an example of a marking.

Another example is to make the tray 1600 sufficiently long such that if it is placed transversely on the tray it will not fit in the entry of the X-ray machine. In this fashion, the tray can only be used in a single orientation.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A method for performing security screening at a checkpoint, including:
    a) providing an X-ray imaging system having a scanning area;
    b) providing a supporting device for supporting articles to be scanned in the scanning area, wherein the supporting device has at least two reference areas manifesting respective X-ray signatures when exposed to X-rays, the X-ray signatures being distinguishable from one another;
    c) placing an article to be scanned on the supporting device;
    d) introducing the article to be scanned in the scanning area while the article is supported by the supporting device;
    e) using the X-ray imaging system for deriving the X-ray signatures of the reference areas and for obtaining an X-ray image of the article while the supporting device is in the scanning area;
    f) using the X-ray signatures to derive X-ray attenuation information from the X-ray image;
    g) using the X-ray attenuation information in determining if the article is a security threat.

2. A method as defined in claim 1, wherein the supporting device includes a tray.

3. A method as defined in claim 1, wherein the supporting device includes a belt.

4. A method as defined in claim 1, wherein the article includes a liquid product.

5. A method as defined in claim 1, wherein the step of using the X-ray signatures includes creating a map in machine readable storage device between grey scale levels and X-ray attenuation information.

6. A method as defined in claim 5, wherein the step of using the X-ray signatures further includes using the map for deriving X-ray attenuation information on the basis of grey scale levels in the X-ray image data.

7. A method as defined in claim 6, wherein the X-ray imaging system includes an array of X-ray detectors, the method including creating a map between grey scale levels and X-ray attenuation information for each detector of the array of X-ray detectors.

8. A method as defined in claim 7, including using the map of each detector for deriving X-ray attenuation information on the basis of grey scale levels in a portion of the X-ray image data generated by the detector.

9. A method as defined in claim 1, wherein the method includes deriving the X-ray signatures from the X-ray image.

10. A method as defined in claim 9, wherein the X-ray signatures are expressed as grey scale levels.

11. An X-ray inspection station for performing security screening on articles, the X-ray inspection station comprising:
- a) an X-ray scanning area where one or more articles are exposed to X-rays;
- b) a supporting device for supporting one or more articles while the articles are exposed to X-rays in the scanning area, wherein the supporting device has at least two reference areas manifesting respective X-ray signatures when exposed to X-rays, the X-ray signatures being distinguishable from one another;
- c) a computer based processing unit for:
  - i) deriving the X-ray signatures of the reference areas and collecting X-ray image data of the article while the supporting device is in the scanning area;
  - ii) using the X-ray signatures to derive X-ray attenuation information from the X-ray image data;
  - iii) using the X-ray attenuation information in determining if the article is a security threat.

12. An X-ray inspection station as defined in claim 11, wherein the supporting device includes a tray.

13. An X-ray inspection station as defined in claim 11, wherein the supporting device includes a belt.

14. A tray for supporting an article while the article is subjected to an X-ray inspection in an X-ray imaging apparatus, the X-ray imaging apparatus including an array of X-ray detectors, the tray including at least two reference areas manifesting respective X-ray signatures that are distinguishable from one another, at least one of the reference areas having an extent such that X-rays passing through the reference area are received by a majority of the X-ray detectors of the array of X-ray detectors.

15. A tray as defined in claim 14, wherein the at least one reference area has an extent such that X-rays passing through the reference area are received by all of the X-ray detectors of the array of X-ray detectors.

16. A tray as defined in claim 14, wherein the tray has a longitudinal axis and a transverse axis, the at least one reference area extending across the longitudinal axis.

17. A belt for carrying an article to be subjected to an X-ray inspection in and out of the scanning area of an X-ray imaging apparatus, the belt including at least two reference areas manifesting respective X-ray signatures when exposed to X-rays, the X-ray signatures being distinguishable from one another.

18. A belt as defined in claim 17, including more than two reference areas manifesting respective X-ray signatures when exposed to X-rays, the X-ray signatures being distinguishable from one another.

19. A belt as defined in claim 17, wherein at least one of the reference areas is elongated and extends across a direction of motion of the belt.

20. A belt as defined in claim 19, wherein the belt is endless.

21. A belt as defined in claim 17, wherein the X-ray imaging apparatus includes an array of X-ray detectors, at least one of the reference areas of the belt having an extent such that X-rays passing through the reference area are received by a majority of the X-ray detectors of the array of X-ray detectors.

* * * * *